(12) United States Patent
Singleton

(10) Patent No.: US 9,173,761 B2
(45) Date of Patent: Nov. 3, 2015

(54) REMOVABLE MEDICAL SUPPORT MECHANISM

(71) Applicant: William Singleton, Wayne, MI (US)

(72) Inventor: William Singleton, Wayne, MI (US)

( * ) Notice: Subject to any disclaimer, the term of this patent is extended or adjusted under 35 U.S.C. 154(b) by 113 days.

(21) Appl. No.: 13/755,350

(22) Filed: Jan. 31, 2013

(65) Prior Publication Data

US 2014/0213946 A1 Jul. 31, 2014

(51) Int. Cl.
*A61F 5/00* (2006.01)
*A61F 5/01* (2006.01)

(52) U.S. Cl.
CPC .................... *A61F 5/0102* (2013.01)

(58) Field of Classification Search
CPC ........... A61B 2017/00792; A61B 2017/00796; A61B 2017/00867; A61B 2017/0409; A61B 2017/0414; A61B 2017/0417; A61B 2017/0419; A61B 2017/042; A61B 2017/0427; A61B 2017/0437; A61B 2017/045; B63C 9/08; B63C 9/02; B63C 9/1255; B63C 11/30; B63C 2009/085; B63C 9/081; B63C 2009/0094; B63C 2009/044; B63C 9/0005; B63C 9/04; B63C 9/18; B63C 9/20; B63C 9/24; A61F 13/04
USPC ...................... 602/16, 20–28; 5/624; 128/882
See application file for complete search history.

(56) References Cited

U.S. PATENT DOCUMENTS

| 3,284,806 | A | | 11/1966 | Prasser | |
|---|---|---|---|---|---|
| 3,786,804 | A | * | 1/1974 | Lewis | 602/16 |
| 6,773,411 | B1 | * | 8/2004 | Alvarez | 602/27 |
| 7,090,651 | B2 | * | 8/2006 | Chiang et al. | 602/5 |
| 8,545,966 | B2 | * | 10/2013 | Vito et al. | 428/167 |
| 2004/0031246 | A1 | * | 2/2004 | Springs | 54/82 |
| 2005/0261617 | A1 | * | 11/2005 | Hall | 602/62 |
| 2008/0161731 | A1 | * | 7/2008 | Woods et al. | 600/595 |
| 2014/0005583 | A1 | * | 1/2014 | Cardinali | 602/5 |

FOREIGN PATENT DOCUMENTS

CA 2270585 * 10/2000

* cited by examiner

*Primary Examiner* — Michael Brown
(74) *Attorney, Agent, or Firm* — Vincent Re PLLC

(57) ABSTRACT

A removable medical support mechanism can be used to protect a body member from injury. The mechanism includes a layer of flexible material providing a constrictive force upon the body member and a mesh layer comprising a plurality of interconnected mesh links. The mesh layer is configured to distribute a force of an impact upon the mechanism, thereby protecting the body member from receiving the force of the impact.

20 Claims, 1 Drawing Sheet

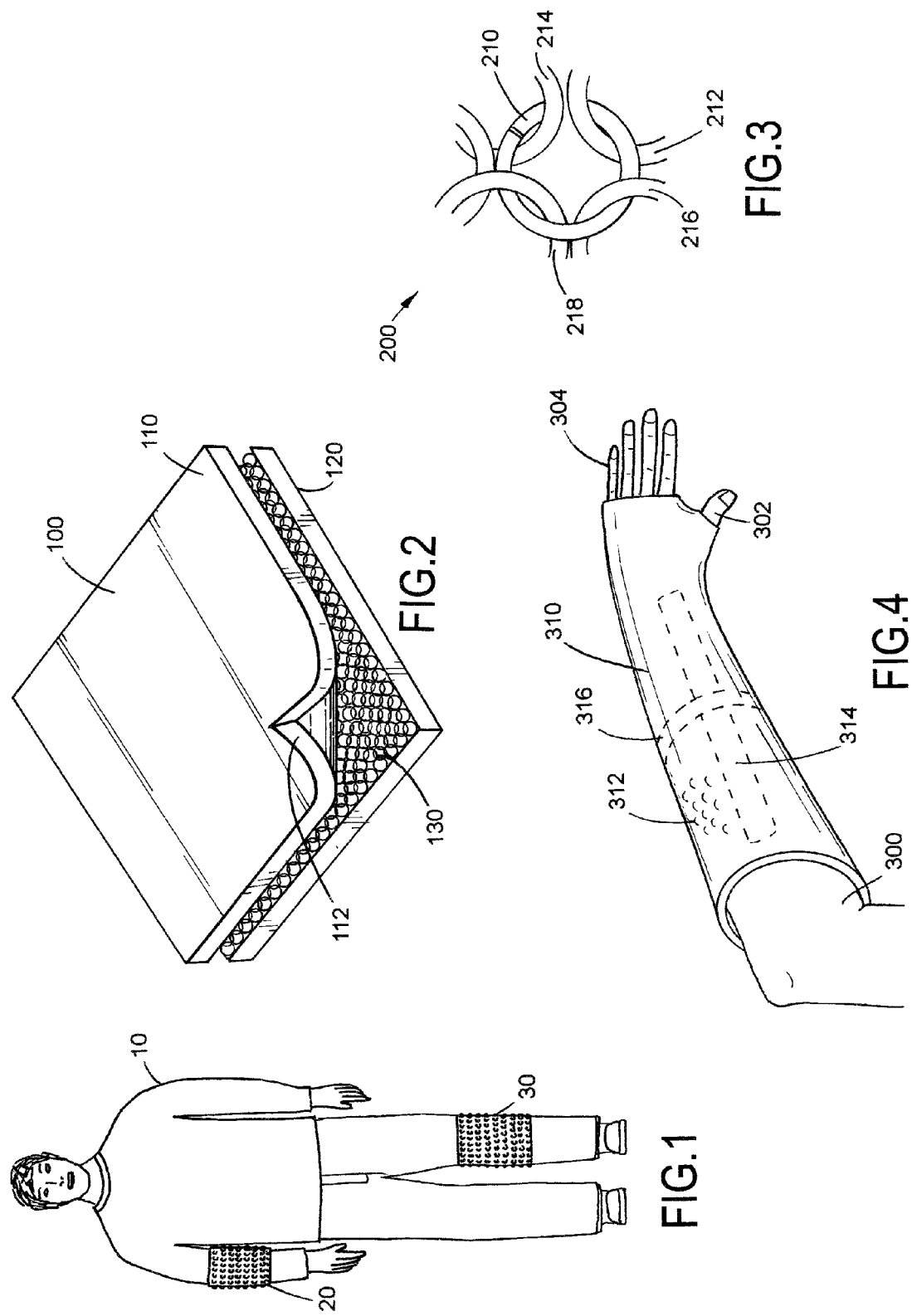

REMOVABLE MEDICAL SUPPORT MECHANISM

FIELD OF THE DISCLOSURE

The present disclosure relates generally to systems and methods for providing a protective covering to the human body. In particular, the disclosure includes combining a first flexible and elastic material with a second material configured to receive and disperse a force impacting upon the material.

BACKGROUND

Presently when human and animal ligaments and tendons are injured; or bones are broken, and need to be immobilized in order to heal, quick-setting plaster of Paris plaster has been one method prescribed. It is excellent at immobilizing a joint and can be inexpensive, but use of a plaster cast is not without limitations. The first is that the prescribing doctor must wait for any swelling to subside prior to its application. Then once in place, it must be removed with a medical saw, destroying it. The skin underneath cannot be accessed during this period. Further, a plaster cast can frequently be inappropriate or impossible for certain fractures, such as a broken toe or a broken bone within a hand.

When the ligaments and tendons attached to a joint are acutely injured and the surrounding joint needs to be immobilized, often the proscribed method of treatment has been to wrap the afflicted joint with cloth or to encase it in plastic encasements. The limbs movement can be unnecessarily restricted from movement but if limited movement is allowed, an unexpected blow or movement can re-injure the afflicted area.

Ligaments and tendons can be chronically inflamed, strained, or otherwise irritated. A person can wear a brace or protective covering to protect the affected area. In one such example, a knee brace can include a pair of straight members adjoined together with a hinge, wherein the hinge permits the knee to bend in a permissible range and in a permissible direction. One embodiment of a protective covering can be constructed of elastic material and can provide a mild constrictive force to isolate or support the body member underneath.

Sporting activities can include impacts or collisions. Athletes push their bodies to various limits, and strain to joints are common. Various forms of protective gear are known to protect an athlete's body from injury. Such protective gear is frequently bulky and restrictive to the athlete's movement or ineffective to protect the athlete from injury.

Animals are subject to injury. Horses riding in rough country can be injured by impacts on sharp underbrush. Dogs used in hunting can come into contact with barbed wire or thickets, or the dogs can come into conflict with the hunted game. Animals frequently have difficulty with conventional casts used to treat injuries such as broken bones.

SUMMARY

A removable medical support mechanism can be used to protect a body member from injury. The mechanism includes a layer of flexible material providing a constrictive force upon the body member and a mesh layer comprising a plurality of interconnected mesh links. The mesh layer is configured to distribute a force of an impact upon the mechanism, thereby protecting the body member from receiving the force of the impact.

BRIEF DESCRIPTION OF THE DRAWINGS

Non-limiting and non-exhaustive embodiments of the present disclosure are described with reference to the following figures, wherein like reference numerals refer to like parts throughout the various views unless otherwise specified.

FIG. 1 is a schematic illustrating a human form wearing the removable medical support mechanism, according to some embodiments of the present disclosure;

FIG. 2 is a schematic illustrating in cross-section an exemplary removable medical support mechanism, according to some embodiments of the present disclosure;

FIG. 3 is a schematic illustrating an exemplary chain mesh construction, according to some embodiments of the present disclosure; and FIG. 4 is a schematic illustrating an exemplary removable medical support mechanism including a rigid support member and an adjustable fitting band, according to some embodiments of the present disclosure.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

In the following description, numerous specific details are set forth in order to provide a thorough understanding of the present disclosure. It will be apparent, however, to one having ordinary skill in the art that the specific detail need not be employed to practice the present disclosure. In other instances, well-known materials or methods have not been described in detail in order to avoid obscuring the present disclosure.

Reference throughout this specification to "one embodiment", "an embodiment", "one example" or "an example" means that a particular feature, structure or characteristic described in connection with the embodiment or example is included in at least one embodiment of the present disclosure. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Embodiments in accordance with the present disclosure may be embodied as an apparatus or method of treatment.

When an individual experiences an injury to either his or her bone or soft tissue, this technique for immobilizing a joint or other body member with a removable medical support mechanism can serve as an alternative to tightly wrapping the afflicted area with cloth or applying a plaster or plastic cast. An exemplary removable medical support mechanism consists of a plurality of layers. According to one embodiment, a flexible elastic material such as neoprene or spandex can be used to provide flexible and comfortable contact with the skin of the wearer. In another embodiment the flexible elastic material can include a number of layers providing different properties in the layers, for example, with a rubberized layer providing elastic properties and with a nylon cloth layer providing soft and breathable contact with the skin of the wearer. Additionally, a mesh layer, such as a chainmail or a chain mesh including a large number of interconnected links, can be used to protect the wearer from impact. A mesh configuration is known to receive an impact and distribute the force of the impact across the links of the mesh. Both the elastic material and the mesh layer can be flexible, permitting free motion of the wearer while protecting and supporting the wearer. By combining a flexible elastic material and a mesh layer, a wearer can enjoy the therapeutic benefits of the elastic material acting as a supportive brace to a covered body member, and the wearer can additionally be protected by ability of the mesh layer to distribute an impact force.

According to one embodiment, the support mechanism can consist of three layers. A first inner layer or soft protective layer can serve as an interface between the patient's skin and a second layer. A second layer can include a mesh layer including interlocking metal rings. These interlocking metal rings form a fabric that resists bending and movement. A third outer layer can include an exemplary neoprene layer containing the other layers and providing an elastic constrictive force to locate the mechanism to the contained body member and providing constrictive support to the member.

An advantage of a technique using a removable medical support mechanism to support soft tissues of the wearer, as compared to conventional treatment, can include permitting controlled movement of the contained member while preventing sudden, severe movements that may re-injure afflicted ligaments or tendons. Traditional treatment can either over restrict movement or allow some movement but not provide the needed protection against sudden unexpected movement.

Similarly, a removable medical support mechanism as disclosed herein can used in place of a plaster or plastic cast. When used as a replacement cast, a removable medical support mechanism can include one or more rigid support members to provide sufficient flexibility and stabilization of the contained body member. Such a removable medical support mechanism has advantages over traditional casts. One advantage of a removable medical support mechanism is that the mechanism can be removable and/or adjustable. In one exemplary use, a loose mechanism can be slid over a freshly injured and swollen body member, and adjustable straps used to tighten the mechanism can be fitted to the swollen member. As the swelling goes down, the adjustable bands can be tightened to the new form of the member or loosened to permit subsequent treatment of the member with a second cast. Another advantage of such a removable medical support mechanism is that the mechanism can significantly lighter than an equivalent plaster cast, protecting and stabilizing the contained member while putting less stress on the member as compared to a heavy cast. A rigid support member can include a metallic or polymer bar, a curved piece of plastic formed in the shape of the contained member, or any other similar material or shape. According to one embodiment, the rigid support member can be situated between layers of the removable medical support mechanism, for example, between the mesh layer and one of the other layers.

Further, a removable medical support mechanism can be used to protect body members that otherwise would not be protectable by a cast. For example, a removable medical support mechanism in a form of a sock can be used to protect a broken toe from impact and further injury. A sock configuration can include a rigid support member further stabilizing the affected toe.

The mesh layer can include links made of different materials and with links of different sizes and link densities. Exemplary mesh designs were historically used in medieval combat armor and are presently used in protective diving suits to protect against shark bites. A removable medical support mechanism does not need to protect against force similar to either combat or shark bites. As a result, lighter, less robust mesh configurations can be utilized. Such a mesh design can include steel links. Other mesh designs can include aluminum links or links made of plastic or other polymer materials. Mesh links for use in a removable medical support mechanism can include a thinner gauge wire than are used in other mesh link configurations.

A removable medical support mechanism can be used in sporting applications. A catcher or an umpire in baseball stand behind the plate, while balls are thrown at high speeds toward the plate. Foul tips can quickly come off the bat and hit the catcher or the umpire with little warning. Known gear to protect the catcher or umpire include rigid plates and heavy facemasks. In the event of a shirt fly ball, the catcher must quickly shed the mask to locate and catch the fly ball. With the removable medical support mechanism of the present application, the catcher could augment or replace some of the heavy, inflexible protective gear currently used with protective gear including a mesh layer capable of receiving and dispersing the force of an impact from a baseball. Such a removable medical support mechanism would be more flexible than current protective gear and could give the catcher an advantage in getting to the fly ball. Similarly, a batter at the plate could wear a removable medical support mechanism around his mid section and back to protect his vital organs and ribs from a wild pitch. Similarly, a quarterback in football, subject to being hit on nearly every play, could wear a removable medical support mechanism to protect his ribs or removable medical support mechanism including a knee brace mechanism to protect against hyperextension of the knee or re-injury of a knee while remaining flexible enough to not hinder the quarterback's motion. A number of sporting applications for a removable medical support mechanism are envisioned, and the disclosure is not intended to be limited to the particular exemplary embodiments provided herein.

Industrial uses for a removable medical support mechanism are envisioned. A worker in a factory might be required to lift heavy or sharp objects. A worker could use a removable medical support mechanism on each forearm to provide for protection against accidental contact with the objects during the workday.

A removable medical support mechanism can be used to protect pets or other animals. A dig or a cat that recently had surgery can be equipped with a removable medical support mechanism in order to prevent the animal from scratching at the stitches from the surgery while protecting the area from impact or abrasion. A horse riding through rough country could be equipped with a removable medical support mechanism on each leg, enabling the horse to travel through dense brush with reduced concern for the horse being injured. A hunting dog chasing a game animal such as a raccoon or a coyote is at risk of the game animal becoming aggressive if cornered. A removable medical support mechanism could be used to provide the hunting dog with some protection from the game animal while still being flexible enough to permit the dog to effectively chase the game animal. A number of uses with animals for a removable medical support mechanism are envisioned, and the disclosure is not intended to be limited to the particular exemplary embodiments provided herein.

FIG. 1 is a schematic illustrating a human form wearing the removable medical support mechanism. A human FIG. 10 with removable medical support mechanism 20 depicted on the right elbow and removable medical support mechanism 30 depicted on the left knee. An alternative removable medical support mechanism could be illustrated on one of the wrists and hands. In one embodiment, removable medical support mechanism 20 depicted on the right elbow can be fastened with Velcro®, snap fasteners, a zipper, or other mechanical fasteners. In another embodiment, removable medical support mechanism 20 can be fastened by wrapping around in several layers and the outer layer fastened in a similar manner to an ace bandage. Mechanisms 20 and 30 are illustrated with a texture indicative of a mesh layer being evident upon the surface of the mechanisms, however, these textures are for illustration only, and a mechanism may or may not have a texture indicating the mesh configuration upon a visible surface of the mechanism.

FIG. 2 is a schematic illustrating in cross-section an exemplary removable medical support mechanism. The layers of the mechanism are illustrated, including a cross sectional patch 100 of the removable medical support mechanism. The bottom layer 110 is worn closest to the patient's skin and provides a barrier between the skin and the mesh layer 130. In one embodiment, this material can be fabricated from a dense form of neoprene or spandex providing a stretching material in contact with the skin, but other materials may be used as well. in some embodiments, bottom layer 110 can include a breathable fabric configured for the comfort of the wearer. A peeled back corner 112 illustrates an example bottom layer 110 being lifted up to provide an exemplary view of mesh layer 130. Mesh layer 130 functions as disclosed herein to provide protection to the wearer against impacts. In one embodiment, it is comprised from metal rings with a cross section 0.040 (1 mm) and an outer diameter of ³⁄₁₆" (4.8 mm), but the size will vary depending upon the desired properties of the device. Layer 120 is the outer layer that covers the medical device and acts as a barrier, preventing the chainmail from catching upon clothing and other item as well as for cosmetic reasons. In one embodiment, layer 120 can include neoprene or spandex to provide stretching or constrictive properties to the removable medical support mechanism. the layers are provided for exemplary illustration only, and are not intended to limit configurations that can be utilized with the disclosed device.

In one embodiment, instead of being comprised of three independent layers, the three layers comprising removable medical support mechanism 100 can be fused or sandwiched together to form a single unit. For example, a neoprene layer could be formed integrally with a pre-existing mesh layer, such that the neoprene fills spaces between the links of the mesh layer. In one embodiment, two layers can be fused together and a third layer can be separate. In one embodiment, two of the layers can be fused together and the third outer layer can be omitted. In another embodiment, the mechanism can include inner and outer layers made of flexible materials, with an additional layer of fabric close to the skin for comfort.

FIG. 3 is a schematic illustrating an exemplary chain mesh construction. Configuration 200 includes a first mesh link 210, and four adjoining mesh links 212, 214, 216, and 218. Each of these mesh links is joined to other links in exactly the same fashion. In this embodiment, Link 210 is made from metal wire, and the wire is bent into the link shape and welded where the two ends of the wire meet. In another embodiment, the links can be molded with no seam. In one embodiment, these links can be fabricated from a material other than metal, such as a plastic or some other polymer. In one embodiment, instead of a weld, a simple non-welded seam is used.

FIG. 4 is a schematic illustrating an exemplary removable medical support mechanism including a rigid support member and an adjustable fitting band, according to some embodiments of the present disclosure. Arm 300 is illustrated with a removable medical support mechanism 310 affixed thereto. Texture 312 is illustrated upon mechanism 310 showing the mesh pattern of mechanism 310 that could be visible upon the surface of the mechanism. Mechanism 310 covers the wrist of the user, such that thumb 302 and fingers 304 extend from an end of the mechanism. Mechanism 310 includes a rigid support member 314 included between layers of the mechanism, such that mechanism 310 can provide stabilization to a broken bone in the arm. One rigid support member 314 is illustrated configured as a bar, for example constructed of light weight aluminum. A plurality of such rigid support members could be used in a single mechanism, and a rigid support member can include any shape or be constructed of an appropriate material, such as plastic. Further, an adjustment band 316 is illustrated within mechanism 310. Adjustment band 316 wraps radially around the arm an can include velcro, a tightening clamp, or any other mechanism known in the art to provide for adjustable constriction of mechanism 310 to arm 300. Adjustment band 316 can be configured to be partially within and between layers of mechanism 310, or adjustment band 316 can be configured to be upon an outer surface of mechanism 310, for example, with straps keeping adjustment band 316 in place sewn into the surface of mechanism 310. A plurality of adjustment bands can be used on a mechanism. A number of exemplary configurations of a removable medical support mechanism are envisioned, and the disclosure is not intended to be limited to the particular examples provided herein.

Rigid support member 314 is illustrated as a straight or nearly straight bar. It will be appreciated that some cast configurations require that a joint of the body member be rigidly held. For example, some casts require that an elbow be contained within the cast. A rigid support member can include bends or more complex geometry configured to the particular body geometry to be contained within the mechanism. Wherein a rigid support member is configured of metal, the member can in some instances be bent by a medical professional to be configured to a particular patient.

A removable medical support mechanism includes a flexible material and/or an adjustment band for providing a constrictive force upon the body member contained within the mechanism. The constrictive force can be appropriate for retaining the mechanism in place. The constrictive force can be appropriate for achieving a medical or therapeutic purpose, for example, to support the body member underneath. The mechanism can include rigid support members and/or a rigid joint hinge mechanism to stabilize a bone contained within the mechanism or to provide support to a joint, permitting movement of the joint in an intended direction and/or through an intended range of movement, respectively. In one exemplary embodiment, a removable medical support mechanism can include auxiliary straps to retain the mechanism in place.

The device disclosed herein can be utilized in a method to protect a body member from a force of an impact. The method can include containing the body member within a removable medical support mechanism, wherein the mechanism provides support and/or protection to the body member contained within the mechanism according to the devices and methods disclosed herein.

Neoprene and spandex are provided as exemplary materials that can provide a layer with stretching properties. These materials are provided as examples of stretching materials. A wide variety of stretching materials are known in the art. The devices and methods disclosed herein can make use of any stretching materials known in the art, and the disclosure is not intended to be limited to the particular examples provided herein.

The disclosure has described certain preferred embodiments and modifications of those embodiments. Further modifications and alterations may occur to others upon reading and understanding the specification. Therefore, it is intended that the disclosure not be limited to the particular embodiment(s) disclosed as the best mode contemplated for carrying out this disclosure, but that the disclosure will include all embodiments falling within the scope of the appended claims.

What is claimed is:

1. A removable medical support mechanism protecting a body member contained within the mechanism, the mechanism comprising:
    a layer of flexible material providing a constrictive force upon the body member; and
    a chain mesh layer comprising a plurality of interconnected mesh rings, wherein each ring is directly attached within the circumference of at least three other rings; and
    wherein the mesh layer is configured to distribute a force of an impact upon the mechanism and protect the body member.

2. The mechanism of claim 1, wherein the layer of flexible material comprises a first layer;
    wherein the chain mesh layer comprises a second layer; and
    further comprising a third layer.

3. The mechanism of claim 2, wherein one of the first layer and the third layer are constructed with neoprene.

4. The mechanism of claim 3, wherein the one of the first layer and the third layer constructed with neoprene is located proximately to skin of the body member.

5. The mechanism of claim 2, wherein one of the first layer and the third layer are constructed with spandex.

6. The mechanism of claim 5, wherein the one of the first layer and the third layer constructed with spandex is located proximately to skin of the body member.

7. The mechanism of claim 1, further comprising a rigid support member configured to stabilize a broken bone within the body member.

8. The mechanism of claim 1, further comprising an adjustment band configured to adjust a constriction force of the mechanism.

9. The mechanism of claim 1, wherein the mesh links are constructed of a metal.

10. The mechanism of claim 1, wherein the mesh rings are constructed of a polymer.

11. The mechanism of claim 1, further comprising a rigid joint hinge mechanism configured to provide support to a joint within the body member.

12. The mechanism of claim 1, wherein the mechanism is configured to protect an athlete playing a sport.

13. The mechanism of claim 1, wherein the mechanism is configured to protect an industrial worker.

14. The mechanism of claim 1, wherein the mechanism is configured to protect an animal.

15. The mechanism of claim 1, wherein the mesh layer is a pre-existing chain mesh layer; and
    wherein the layer of flexible material is formed around the pre-existing mesh layer.

16. A removable medical support mechanism protecting a body member contained within the mechanism, the mechanism comprising:
    an inner layer of flexible material;
    an outer layer of flexible material; and
    a chain mesh layer located between the inner layer and the outer layer comprising a plurality of interconnected mesh rings, wherein each ring is directly attached within the circumference of at least three other rings; and
    wherein the mesh layer is configured to distribute a force of an impact upon the mechanism and protect the body member.

17. A method to protect a body member from an impact force, comprising:
    containing the body member within a removable medical support mechanism, the mechanism comprising:
        a layer of flexible material providing a constrictive force upon the body member; and
        a chain mesh layer comprising a plurality of interconnected mesh rings, wherein each ring is directly attached within the circumference of at least three other rings and wherein the mesh layer is configured to distribute a force of an impact upon the mechanism and protect the body member.

18. The method of claim 17, wherein the body member comprises an elbow.

19. The method of claim 17, wherein the body member comprises a knee.

20. The method of claim 17, wherein the body member comprises a wrist.

* * * * *